United States Patent

Lo

[11] Patent Number: 5,135,007
[45] Date of Patent: Aug. 4, 1992

[54] MEANS AND METHOD FOR SEMI-AUTOMATICALLY ATTENUATING SOUND IN THE EARS

[76] Inventor: Nahm V. Lo, 1421 Harrison Ave., Des Moines, Iowa 50314

[21] Appl. No.: 698,398

[22] Filed: May 10, 1991

[51] Int. Cl.$^5$ ............................................. A61F 11/10
[52] U.S. Cl. .................... 128/864; 128/846; 128/866
[58] Field of Search ............... 128/864, 865, 866, 867, 128/868, 857, 846; 2/423

[56] References Cited

U.S. PATENT DOCUMENTS

| | | | |
|---|---|---|---|
| 2,476,589 | 11/1946 | Driskill | 128/152 |
| 3,505,999 | 4/1970 | Harvey et al. | 128/865 |
| 3,844,580 | 10/1974 | Scherenberg | 128/865 X |
| 4,700,410 | 10/1987 | Westgate | 2/423 |
| 4,896,679 | 1/1990 | St. Pierre | 128/865 |
| 4,913,165 | 4/1990 | Fishgoyt | 128/865 |

FOREIGN PATENT DOCUMENTS 8803010  5/1988  World Int. Prop. O. .......... 128/864

Primary Examiner—Robert A. Hafer
Assistant Examiner—Sam Rimell
Attorney, Agent, or Firm—Zarley, McKee, Thomte, Voorhees, & Sease

[57] ABSTRACT

A system to block ears to suppress or attenuate sound from entering the ears includes ear blocking structures which are movable between a first position which does not completely block the auditory canals of the user, and a second position which causes the auditory canals to be substantially blocked. An actuator is connectable to the ear blocking members and moves the ear blocking members to the second position upon instruction. The instruction is created by the user causing a switch to be closed signaling the actuator to operate. The ears are semiautomatically blocked without the requirement of the user to manually insert an earplug into the ear, or place an ear cup over the ear.

18 Claims, 3 Drawing Sheets

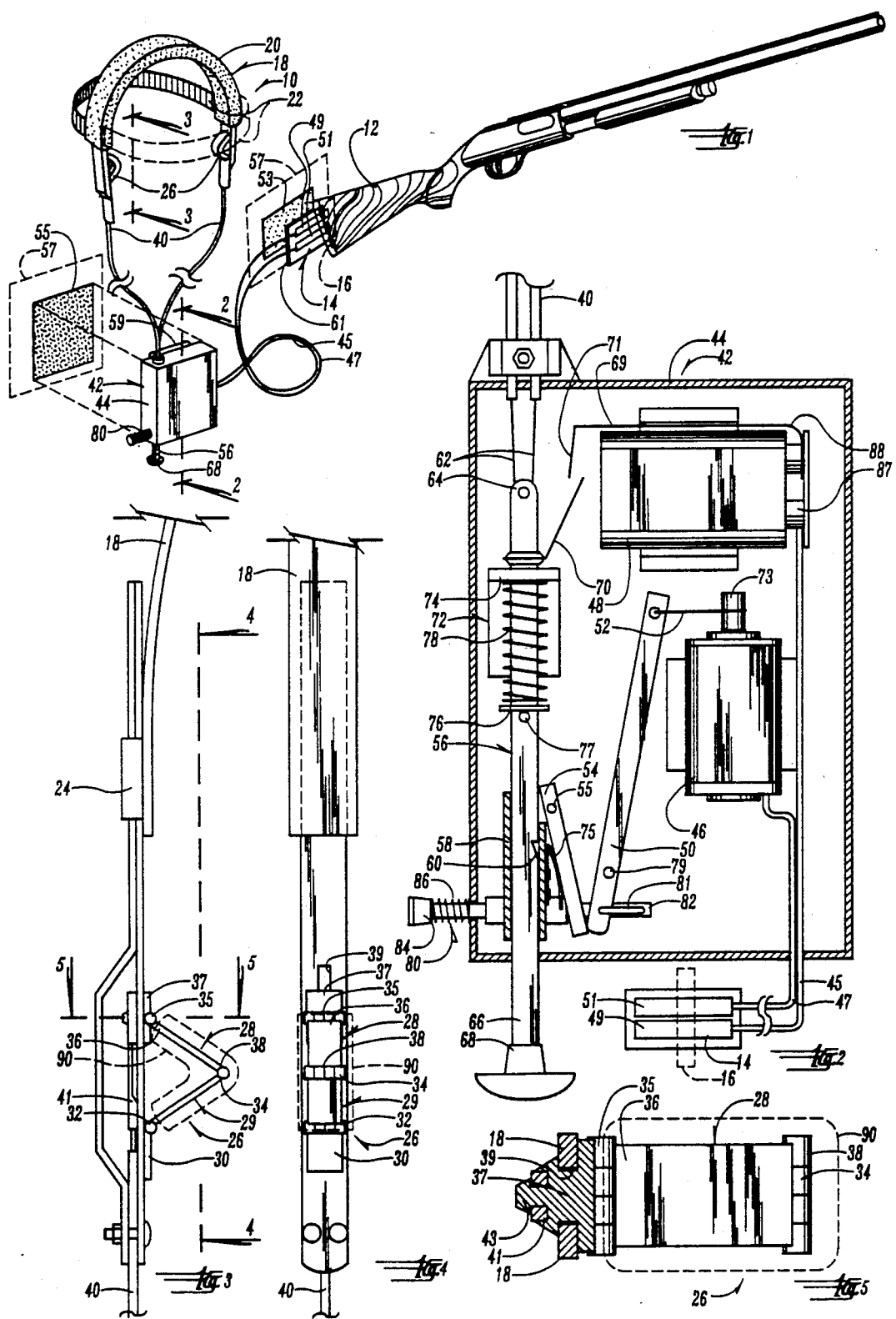

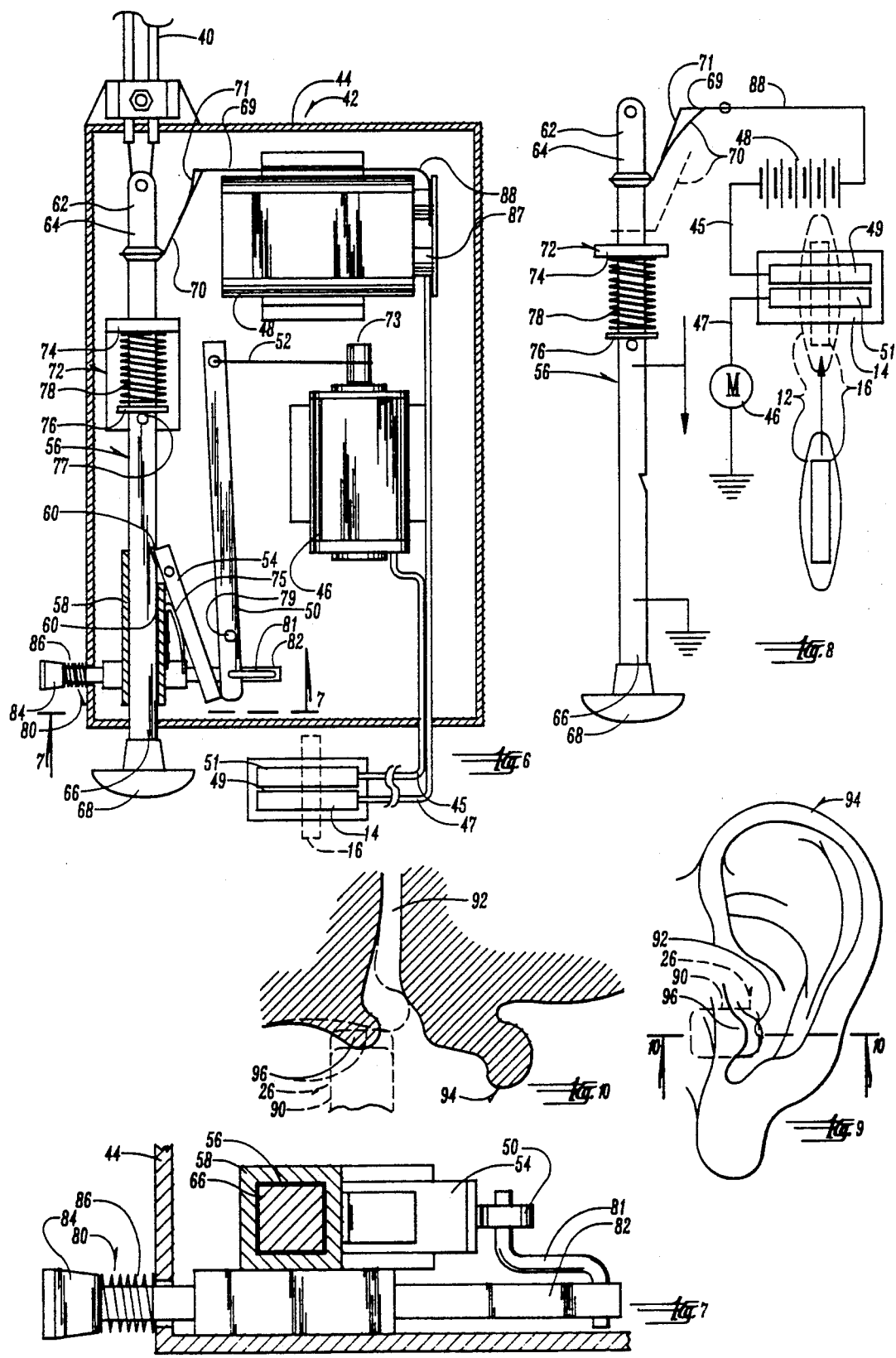

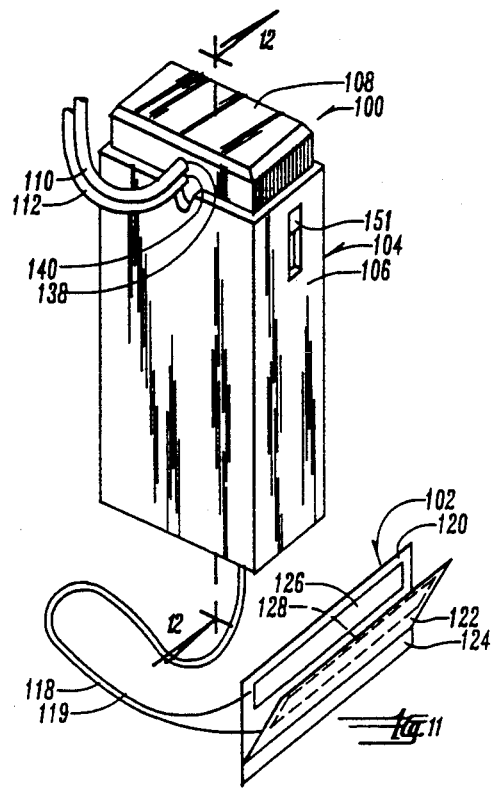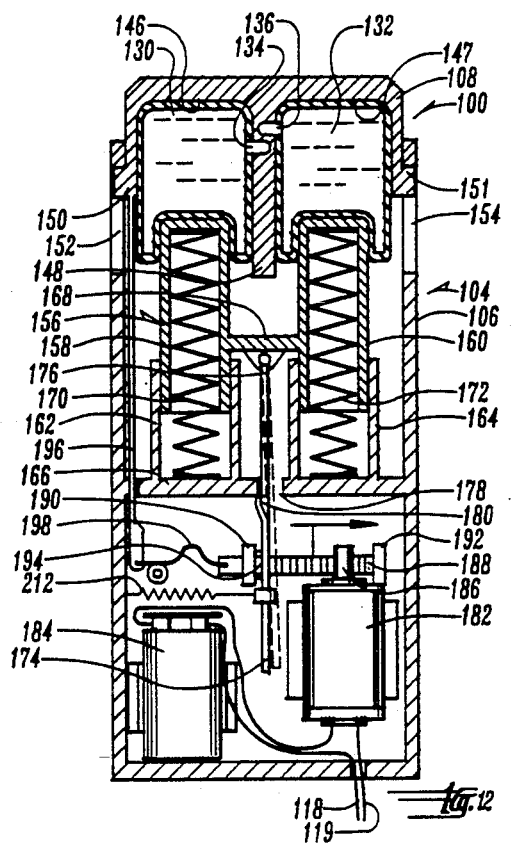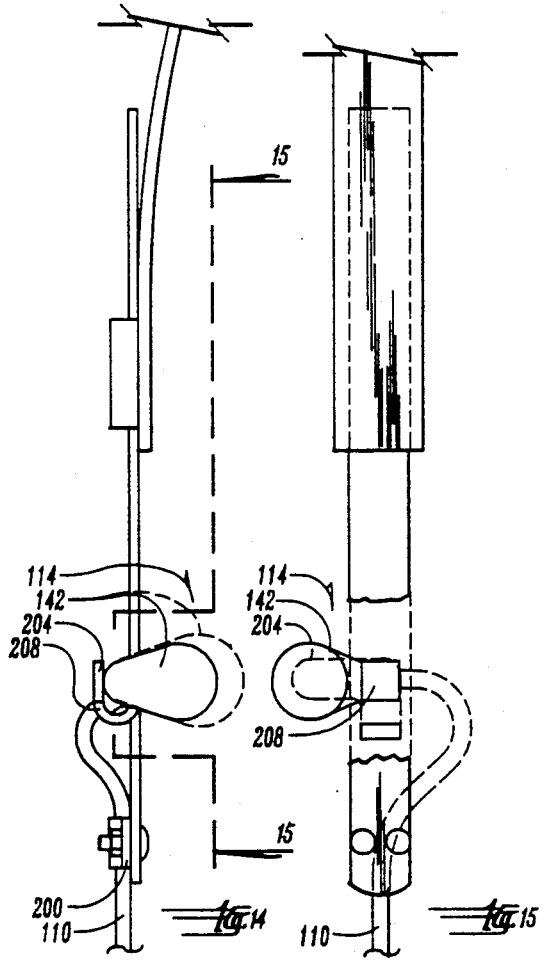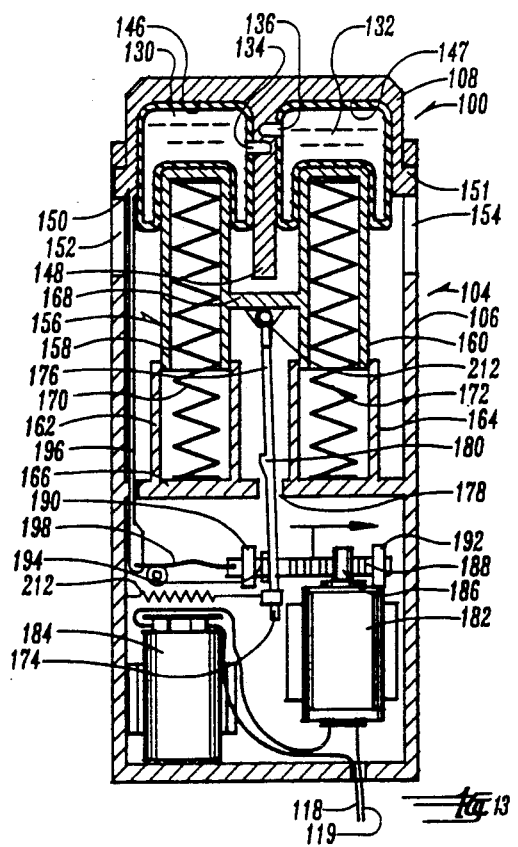

MEANS AND METHOD FOR SEMI-AUTOMATICALLY ATTENUATING SOUND IN THE EARS

BACKGROUND OF THE INVENTION a. Field of Invention

This invention relates to ear blocking devices, and in particular, to semiautomatic blocking of a person's ears to attenuate sound in the ears.

b. Problems in the Art.

When one operates equipment which emits loud sounds, a user exposes himself to the danger of doing permanent damage to his ears. If the decibel level of a sound, even for short duration, exceeds a certain level, the mechanical pressure waves (which comprise the sound) can traumatize the tissues or bone structures of the human ear, and physically damage them.

In many instances it is therefore appropriate, if not necessary, to protect against potential for such damage. Some conventional attempts to diminish the level of sound which reaches the critical parts of the ears are the use of ear cups, ear coverings, or earplugs. In the case of ear cups, a head set with a head band is usually used to help mount and position the cups to the ears. The attempt is to seal the cups around the perimeter of the ear to deter the mechanical pressure waves from entering directly into the auditory canal and then on to the ear drum, or further into the fragile bones of the middle ear or the fragile components of the inner ear. The user must therefore take care to adjust the ear cups to achieve the best possible seal over the ears. Because of the size of the ear cups, this type of arrangement is somewhat cumbersome. It requires one or two hands to position the device on the head around the ears, as well as the manual removal of the device when unobstructed hearing is desired. It can also be difficult to carry or store conveniently.

Ear plugs are more convenient in the sense that they are usually small, and not as cumbersome as ear cups. They can be more easily transported, maneuvered, and stored. They still require, however, the user to manually place them in the ear to plug the auditory canal, again to stand in the way of the mechanical pressure waves of the loud noise from damaging parts of the ear. They also must be manually maneuvered in and out of the ears.

Many times, the operator of the equipment does not wear earplugs for various reasons. The user may forget to place the earplugs in the ears. Placing the earplugs in the ears may be time consuming as well as inconvenient for the user. For example, in skeet shooting, the skeet shooter may find it an inconvenience to repeatedly place earplugs in his ears when he is ready to shoot. The shooter may not want to spend the time and energy to plug up his ear. Therefore, he may rationalize that the earplugs are more trouble than they are worth, but prolonged exposure to loud noises may cause hearing loss or deafness. As such, the user may later regret not wearing his earplugs.

An additional example is the shooting of firearms during hunting. The excitement of the moment or the necessity of quick action may cause the user to neglect placing the earplugs in his ears. The hunter may not want to wear an earplug continuously during hunting because it is important for him to be able to listen for the telltale sign of the animal that he is hunting. When he spots his game, the hunter does not have time to place the earplugs in his ear. He must shoot immediately. This exposes the hunter's ear to discharge of the gun.

If the user continuously wears earplugs, the ability to communicate verbally is diminished. This can be significant, and even dangerous, in several situations.

There is therefore a real need for a device or system which improves over or solves the deficiencies and problems in the art. There is a need for a way to protect a user's ear which is more convenient than current methods. There is also a need for a system of protecting the user's ear which does not require complete reliance on the user to manually place the devices and remove the devices when desired.

Therefore, a primary objective of the present invention is the provision of means and method of semiautomatically attenuating sound in the ears which improves over the state of the art.

A further object of the present invention is to provide a means and method as above described which automatically protects a user's ears whenever the user attempts to operate a device which produces loud sounds.

Another objective of the present invention is the provision of means and method as above described which deters or prevents injury to the user's ears when the user operates a device which produces loud sounds.

Still another objective is the provision of means and method as above described which can be used in such a manner as to not unnecessarily interfere with the user or the operation of the user's equipment.

Still another objective is the provision of means and method as above described which is compact so as not to interfere with the wearing of head wear by the user.

A further objective of the present invention is the provision of a means and method as above described which prevents the user from directly exposing his/her ears to loud sounds, yet is inexpensive to manufacture, economical, durable, reliable, and easy to operate and maintain.

These and other objectives, features, and advantages of the invention will become apparent from the following description of the invention.

SUMMARY OF THE INVENTION

A semiautomatic system is provided for protecting a user's ears from the sound made during the operation of a device. A headset, including left and right ear blocking means, is positionable on a user's head. An actuator is operatively connected to the ear blocking means by a connection means and is mountable to the user. The actuator is controlled by the user. When the actuator is actuated, it moves the ear blocking means to a position which causes the blockage of the auditory canals of both ears of the user.

Control of the actuator is accomplished by a switch means. Operation of the switch means is accomplished by a switch control or closure means which can be positioned at, near, or away from the actuator. The switch means closes to connect power to the actuator only upon activation of the switch means. When the switch means between a power source and actuator is closed, the actuator causes the ear blocking means to extend outward toward the ears to cause blockage of the auditory canals of the ears.

In the preferred embodiment, the invention enables the user of such things as a firearm to latch the ear blocking means out of the shooter's ears before the firing of the gun. The switch means and the actuator could be positioned or worn on the user's clothing. By bringing the butt of the user's gun into abutment with the switch control means, the switch means closes, and the actuator operates causing the ear blocking means to extend outward forcing a part of the user's ear to cover its corresponding auditory canal, thereby diminishing the effect of a high decibel sound from entering the interior of the shooter's ears and thus protecting the shooter from the sound of the gun's discharge.

The invention is therefore semiautomatic in the sense that it requires some manual movement of the user to close the switch means. Thereafter, the actual blockage of the user's ears is automatic. The user does therefore not have to manually position anything at or around the user's ears, but relies instead upon the quick, easy, and reliable closing of a switch after previously placing the ear blocking means in position adjacent to the ears.

BRIEF DESCRIPTION OF THE DRAWINGS

FIG. 1 is a perspective view of a preferred embodiment of the invention shown in association with a firearm.

FIG. 2 is an enlarged sectional view taken along line 2—2 of FIG. 1.

FIG. 3 is an enlarged partial view taken along line 3—3 of FIG. 1.

FIG. 4 is taken along line 4—4 of FIG. 3.

FIG. 5 is taken along line 5—5 of FIG. 3.

FIG. 6 is similar to FIG. 2 except it shows the status of the actuator according to the invention in a position where ears of the user are not blocked and the switch means is not closed. In comparison, FIG. 2 shows the actuator in position where the switch means is closed, actuating the actuator, which in turn blocks the user's ears.

FIG. 7 is an enlarged partial sectional view taken along line 7—7 of FIG. 6.

FIG. 8 is a schematic and diagrammatical view of the electrical circuitry according to the preferred embodiment of the invention.

FIG. 9 is a side elevational view of a human ear diagrammatically showing how the ear is blocked by the invention.

FIG. 10 is an enlarged sectional view taken along line 10—10 of FIG. 9 showing with more specifically of how the preferred embodiment of the invention blocks the human ear.

FIG. 11 is a perspective view of an alternative embodiment for the present invention. FIG. 11 shows a switch means and actuator means, but does not show the headset or ear blocking means.

FIG. 12 is a sectional view taken along line 12—12 of FIG. 11 showing the actuator device set to position where the ear blocking means do not block the user's ears.

FIG. 13 is essentially similar to FIG. 12 except showing the actuator device in the position where it blocks the user's ears.

FIG. 14 is a side elevational view of a portion of a user headset showing the ear blocking means of the embodiment of FIG. 11.

FIG. 15 is a sectional view taken along line 15—15 of FIG. 14.

DESCRIPTION OF THE PREFERRED DESCRIPTION

To assist in a better understanding of the invention, a preferred embodiment will now be described. Reference numerals will be used to indicate specific parts or locations in the drawings. The same reference numerals will be used to indicate the same parts and locations in all the drawings, unless otherwise indicated.

Referring to the drawings, one embodiment of a semiautomatic means for alleviating sound in a user's ears according to the present invention is generally designated by the reference numeral 10. The device 10, in this preferred embodiment, is designed for use with a gun 12. The gun 12 is shown in FIG. 1 in a position where its end or butt is in contact with switch 14. It is to be understood that the contact of the butt of gun 12, which includes will be called a closure 16 which is made of a conductive material, with switch 14 is the required manual movement to close switch 14. Closing of switch 14 in turn causes closure of the auditory canals in both of the user's ears, as will be explained further below.

The automatic earplug device 10 includes a headset 18 which is wrapped by a rubber guard 20. Headset 18 is basically a U-shaped member which is resilient so that opposite ends can be stretched apart to allow its insertion over the head of the user. The rubber guard protects the user's head from the headset 18. Optionally a head band 22 can also be utilized to maintain the position of device 10 on the user's head. Band 22 can be made of a strap-like material and basically would be adjustable in size to fit around the circumference of the user's head perpendicularly to head set 18. It would be positioned approximately around the forehead and back of the head of the user. In the preferred embodiment, the front or back of head band 22 could be made of straps which are separable from one another, but have some sort of a securement means which has hook and loop material (e.g. Velcro), to allow adjustment for various sized heads, and to assist in the securement of head set 18 to the user's head.

As can be easily understood from FIG. 1, the head set can be pre-positioned on a user's head. The headset 18 has a pair of adjustments 24 (see FIG. 3) for fitting the automatic earplug device 10 on the user's head. As can be seen in FIG. 3, adjustments 24 simply allow for the length-wise adjustment on either side of head set 18 to accommodate different users' head sizes, and to accurately position the ear blocking means, which will now be described.

In FIG. 1 it can be seen that each ear blocking means 26 comprises a triangularly shaped member which is positioned on head set 18 generally in the position of the auditory canals of left and right user's ears. As shown in FIG. 1, actuating cables 40 extend downwardly from each ear blocking means 26 to an actuator 42. It can also be seen that electrical wires 45 and 47 extend from the actuator 42 to switch means 14. Each wire 45 and 47 is connected to separated electrically conducting strips 49 and 51, which are spaced apart in a parallel relationship on an insulating surface of switch means 14.

FIG. 1 also shows a lever arm 56 extending out to a handle 68 with respect to actuator 42. A reset button 80 is also shown extending out of actuator 42.

As will be explained in more detail below, ear blocking means 26 are normally in an inwardly extended position such as shown in FIG. 1. In other words, they are raised away from the adjacent portions of head set 18. Lever arm 56 is in an extended or outwardly biased position when ear blocking means 26 are in their extended position as shown in FIG. 1.

In the preferred embodiment, housing 44 of actuator 42 encases the working components of actuator 42 except for the outer ends of lever arm 56 and reset button 80. Switch 14 can be placed at a variety of locations, even at a location somewhat remote from actuator 42. In the preferred embodiment, the side of switch 14 opposite the strips 49 and 51 could be removably secured to a desired location. For example, a pad or patch 53 of hook or loop material could be sewn onto a user's jacket 57 at the location around the user's shoulder where the butt of gun 12 would generally be placed during firing. A patch 61 on the back of switch 14 could include hook or loop material so that it could be easily attached to patch 53 on jacket 5.

Similarly, a patch 55 of hook or loop material could be sewn or otherwise secured to user's jacket or shirt 57 at another location. A pad 59 of hook or loop material could also be utilized on the back of housing 44 of actuator 42 to allow removable placement of the entire actuator 42 on the user. In the preferred embodiment, positioning of patch 55 would be on the front of the user's jacket but in a position away from patch 53 corresponding with switch 14. It is to be understood, of course, that the relative positioning of the various pieces can be adjusted according to desire.

FIG. 2 shows in detail the contents of actuator 42. It is to be understood that when closure 16 on the butt of gun 12 electrically connects or shorts strips 49 and 51 on switch 14, the electrical circuit in actuator 42 can be actuated, if lever arm 56 is preset correctly. The actuation of actuator 42 will cause movement of shielded cables 40 which in turn will operate ear blocking means 26 to move from the extended position in FIG. 1 to a position where they are flattened against the insides of head set 18. This will un-block the auditory canals of both of the user's ears.

The movement of the cable 40 is controlled by means of actuator 42. As seen in FIG. 2 the actuator 42 is comprised of motor 46 operatively connected to a power source 48 by the switch 14. The power source has positive and negative terminals 87 and 88. The motor 46 is also connected to a bar 50 by means of string 52. The bar 50 is pivotally mounted at 79 to the enclosure 44. The preferred embodiment power source 48 is a nine volt DC battery. Additionally the motor is available from Maburchi and is a DC motor capable of operating on the current and voltage supplied by the 9 volt DC battery.

The actuator 42 is further comprised of a latch arm 54 rotatable mounted at 55 to the enclosure 44 and of lever 56 which is surrounded by a guide member 58 which is attached to the enclosure 44. There is a notch 60 located on one side of the lever 56. The ends 62 of cables 40 are attached to one end 64 of the lever 56 within the enclosure 44. A second, opposite end 66 of the lever 56 extends outside of the enclosure 44. At that end of the lever is a handle 68. Attached to end 64 of the lever is a conducting member 70. It is to be understood that conducting member 70 is grounded.

Also, within the enclosure is a stop means 72. The stop means 72 comprises a small platform 74 mounted to the enclosure 44. The platform 74 has an opening to allow the lever 56 to slide through.

The stop means 72 is also comprised of an affixed ring 76 surrounding the lever 56 so as to prevent the lever 56 from sliding completely through the opening in the platform 74. It also captures and holds a spring 78 placed around the lever 56 between the platform 74 and the ring 76. Spring 78 pushes away from platform 74 against ring 76. Ring 76 abuts against pin 77 that is rigidly connected to lever arm 56. Spring 78 therefore urges lever 56 to extend outwardly of enclosure 44, and also pulls ends 62 of cables 40 into enclosure 44.

A reset button 80 is connected to the bar 50. The reset button 80 is comprised of rod 82 pivotally connected to the bar 50 (by pivotally connected piece 81), the rod 82 extending into the enclosure 44. The rod 82 has a handle 84 on one end and a spring 86 to bias the handle end of rod 82 outwardly. As can be seen in FIG. 2, lever 56 slideably moves through apertures in guard member 58 and platform 74 of stop means 72. It is normally biased by spring 78 in an outward position which draws ends 62 of cables 40 into housing 44 of actuator 42. Ear blocking means 26 are extended when lever arm 56 is in that position.

However, if lever arm 56 is pushed inwardly of housing 44 and notch 60 reaches the upwardly biased latch arm 54, lever arm 56 will latch and lock in that pushed-in position. Spring 78 will be compressed. Also, ends 62 of cables 40 will have been pushed outwardly which flattens ear blocking means 26.

FIG. 2 illustrates that the battery power source 48 is communicated by wire 45 to strip 49 on switch 14. Strip 51 on switch 14 is communicated by wire 47 to motor 46. When closure member 16 electrically shorts the gap between strips 49 and 51, the electrical pathway between battery 48 and motor 46 is closed.

FIG. 2 also shows how conductor 69 is connected to the negative connection 88 of battery 44 and extends along side of battery 48 to a bent end 71. The conductor 70, as previously described, is connected to lever arm 56, which in turn is grounded. Any contact between end 71 and conductor 70 concurrently with the shorting of enclosure 16 across strips 49 and 51 will complete the circuit between battery 48 and motor 46 and cause motor axle 73 to rotate in a clock-wise direction and wind-up string 52 on axle 73. This will pull down on bar 50 at one end, which will allow the other end of bar 50 to push up on latch arm 54. Therefore, if lever arm 56 is latched at notch 60, it will be released and pushed outwardly by spring 78, pulling the wires of shielded cables 40 inwardly and extending ear blocking means 26.

FIGS. 3-5 more particularly show the structure of ear blocking means 26. First, second, and third sections 28, 29, 30 make up the portion of means 26 which blocks the ear. Third section 30 is rigidly attached to head set 18. A hinge 32 exists between the third section 30 and second section 29. A hinge 34 is positioned between second section 29 and first section 28. Finally a hinge 35 comprises the junction between first section 28 and a carriage block 37. By referring to FIG. 4, can be seen that there is a slot 39 in head set 18. By referring to FIG. 5 can be seen that carriage block 37 is shaped so that it is retained but slideable within slot 39. Still further, carriage block 37 has an end 43 to which is connected cable connector 41, which in turn is connected to cable 40.

Referring back to FIG. 3, it can therefore be seen that when cable 40 is pulled downwardly (into housing 44 of actuator 42), carriage block 37 is also pulled downwardly causing first and second portions 28 and 29 to hinge upwardly and outwardly to the position shown in FIG. 3. However, when cable 40 is moved upwardly (by pushing in and latching lever arm 56) cable 40 pushes carriage block 37 upwardly which would flatten down first and second sections 28 and 29 of ear blocking means 26.

FIG. 6 shows the relationship of the components of actuator 42 when lever arm 56 is pushed in and latched. It should be particularly noticed that when this occurs, bar 50 is in a position whereby string 52 connected between the end of bar 50 and axle 73 of motor 46 is extended or unwound. Flat spring 75 biases latch arm 54 downwardly to hold bar 50 in this position.

It should be further noted that reset button 80 can be utilized to ensure that bar 50 is moved to the position shown in FIG. 6 and that string 52 is unwound from axle 73 to the position shown in FIG. 6. This is accomplished by pushing handle or button 84 towards housing 44 of actuator 42 against the spring 86. This action will in turn pull the end of bar 50 to which reset rod 82 is attached around pivot 79 so that the end of bar 50 connected to string 52 is in position as shown in FIG. 6. Once handle 84 is released, spring 86 returns reset button 82 to a normal position and connection member 81 pivots so it does not disrupt bar 50, which is held in the position by flat spring 75 and latch arm 54.

FIG. 8 shows schematically the electrical circuit of the invention. It also illustrates how the electrical circuit is opened and closed. When lever arm 56 is in the position that conductor 70 and conductor 71 are in contact, and when closure 16 on rifle butt 12 shorts out strips 49 and 51, the complete circuit is made. When this occurs, motor 46 will operate to wrap string 52 around axle 73 and pull the end of bar 50 connected to string 52 towards axle 73. This will in turn raise the opposite end of bar 50 to release latch arm 54 from notch 60 and lever arm 56. The force of spring 78 will then cause lever arm 56 to move outwardly of housing 44. This causes conductors 70 and 71 to move along one another and finally separate, as shown in dashed lines for conductor 70 in FIG. 8. Once this occurs the electrical circuit is broken and motor 46 stops to preserve the power of the battery or to prevent binding or stalling.

FIG. 7 shows in more detail the operation and structure of reset button 84. It shows with more detail how connection 81 is hinged between rod 82 of reset means 80 and the end of bar 50.

FIG. 9 and 10 depict in more detail how ear blocking means 26 actually accomplishes blocking of the auditory canal 92 of ear 94. In FIG. 9, your blocking means 26 is shown in broken lines. It is depicted as one solid rectangle illustrating how the hinged first and second sections 28 and 29 are covered with a rubber guard 90. Blocking means 26 is in line with what is referred to as the tragus 96 of the human ear (a small flap of skin-covered cartilage) generally over the entrance to the auditory canal 92, or at least partially blocks the auditory canal 92.

As can then be seen in FIG. 10, when the invention 10 is operated to move ear blocking means 26 from the flat position to the extended position, blocking means 26 will move to, contact, and then push tragus 96 down and across auditory canal 92 to block access to it. This effectively accomplishes what ear plugs are to accomplish. However, it does so without any plug or other structure being inserted into the auditory canal 92 by using a portion of the ear 94 itself to block canal 92.

Typical operation of invention 10 as set forth above will now be described. First, closure member 16 has to be attached by adhesive or other means to the butt of gun 12. Then pad 53 and pad 55 must be attached to the user's jacket or clothing in the desired positions. Head set 18 is then manually positioned on the user's head so that both ear blocking means 26 are in abutment with the tragus 96 for each of the user's ears; so that the user can confirm that when extended the ear blocking means 26 push the tragus of each ear into the auditory canals of each ear. The head set 18 is then adjusted or tightened in place. If head band 22 is used, it is also adjusted and tightened into place.

Thereafter, actuator 42 is secured to pad 55 on the jacket, and switch 14 is secured to pad 53 on the jacket. It is generally desired that strips 49 and 51 of switch means 14 be secured in a horizontal position so that when gun 12 is brought into a firing position against switch 14 closure 16 will be generally vertical and therefore electrically short strips 49 and 51.

If the user desires to have his/her ears blocked at all times, invention 10 is left in that configuration. However, if it is desired to move ear blocking means 26 to the flattened position so that the user can freely hear, actuator 42 is set by pushing handle 68 of lever arm 56 inwardly towards housing 44 until lever arm 56 latches on notch 60 by latch arm 54. Again this position is shown in FIG. 6.

The lever 56 is manually forced into the enclosure 44 so as to compress the spring 78 between the ring 76 and the platform 74 and latch 54 latches the lever 56 in that position. The handle 68 is used to assist the user in latching the lever 56.

When the lever 56 is latched, the cable 40 forces the first and second sections 28 and 29 of each ear blocking member 26 to slide along the headset 18 away from the lower section 30 causing each earplug 28 to retract from the user's ears. In addition, the conductor 70 (see FIG. 6) attached to the lever 56 comes in contact with the end 71 of conductor 69 which is in turn attached to negative terminal 88 of the power source 48. This grounds the terminal 88.

Once latched, the lever 56 can be released if the user closes the switch 14 causing the circuit between the power source 48 and motor 46 to close. This is done by raising gun 16 to the user's body, and particularly placing closure 16 across strips 49 and 51 of switch 14. When the switch 14 is closed, the motor 46 rotates and shortens, by winding, the string 52, which is attached to the bar 50 which is pivotally mounted to the enclosure 44. The bar 50 pivots causing the latch 54 to release. When the latch 54 is released, the stop means 72 forces the lever 56 into its un-latched position and the conductor 70 loses contact with the end 71 of conductor 69 causing the motor 46 to stop. The cable 40 is retracted causing the first and second sections 28, 29 of each ear blocking means 26 to slide toward the third section 30 along the headset 18. The ear blocking means 26 then extend inwardly forcing the user's ear flaps (the tragus in each ear) to block the user's auditory canals. Once lever arm 56 is un-latched and pushed outwardly, ear blocking means 26 will maintain blockage of user's ears until either lever arm 56 is relatched, or the head set 18 is removed. If the lever arm 56 is re-latched, reset button 80 can be pushed to assist in returning the bar 50 to its position in FIG. 6 before the closure of the switch 14, and also to completely unwind the string 52 from the motor 46.

A second preferred embodiment of the invention can be seen illustrated at FIGS. 11-15. This embodiment will also be described with regard to operation with a gun, such as a rifle or shotgun. It is to be appreciated, however, that the invention could also be utilized with other devices or even used to selectively block or open a person's ears by pushing the switch means. It is to be understood that the basic principles of the first previously described embodiment also apply to this embodiment.

FIG. 11 illustrates the switch 102 and actuator 104 for an embodiment useful for a hunter or skeet shooter, according to the present invention. A case 106 houses the working elements for actuator 104. A single push button 108 is utilized to set actuator 104. Hoses 110 and 112 are connected to ear blocking means 114 and 116 (only means 114 is shown, see FIGS. 14 and 15).

Electrical wires 118 and 119 are connected to switch 102.

As shown in FIG. 11, switch 102 is comprised of panel 120 and a hinged biased panel 122. Panel 122 is held in a normally angled-away position from panel 120, but is hingably attached along line 124 to panel 120. Wire 119 is electrically connected to conducting strip 126 on panel 120. Wire 118 is electrically connected to conducting strip 128, secured on the inside surface of panel 122.

Switch 102 is closed by moving hinging panel 122 into contact with 120. Conducting strips 126 and 128 then form an electrically conducting path through switch 102. In the case of the gun, all that is required is that switch 102 be attached to the shooting shoulder of the user, and then the butt of the gun brought against panel 122, in turn flattening it against panel 120. Once pressure is released from panel 122, it hinges away and disconnects the electrical connecting path through switch 102.

Like the first embodiment described previously, actuator 104 functions to block a user's ears when switch 102 is closed. Also like the first embodiment, the ear blocking means are normally in an outward or ear blocking position. The embodiment 100 therefore must be set by pushing push button 108 downwardly. As will be described below, this will cause the ear blocking means 114 and 116 (not shown) to move to a position which will not block the user's hearing and ear blocking means 114 is positioned directly over the tragus of the user's ear. Blocking of the ears is then automatically accomplished once switch 102 is closed.

It is to be understood that in embodiment 100, the means and method by which the user's ears are blocked is the primary difference from embodiment 10. In order to provide a different and what might be considered by some a more comfortable system for accomplishing ear blocking, rubber balloons are expanded by filling them with water (or other liquid), which expands the balloons and blocks the user's ears.

By referring to FIGS. 12-15, this system is shown in more detail. A fluid circuit exists for each ear of the user. As seen in FIG. 12, fluid reservoirs 130 and 132 are positioned just below and inside push button 108. Reservoirs 130 and 132 can be made of resilient rubber (or other such material) and are substantially filled with water.

Conduits 134 and 136 are communicated into the interior of reservoirs 130 and 132 by means known within the art. Conduits 134 and 136 then extend through push button 108 to form outlet openings 138 and 140. (See FIG. 11)

By referring to FIG. 11, hoses 110 and 112 are connected to openings 138 and 140. By then referring to FIGS. 14 and 15, it can be seen that hoses 110 and 112 each extend to a small balloon 142 and 144 respectively. (Only balloon 142 is shown—the structure for the opposite ear is basically the same.)

Each fluid system therefore comprises a balloon 142 or 144, a hose 110 or 112, a conduit 134 or 136, and a reservoir 130 or 132. The entire fluid circuit is concealed from leakage by sealing means and substances known within the art. Balloons 142 and 144 can be made of any resilient yet fluid tight rubber-type material. Hoses 110 and 112 can be made of any fluid tight material such as plastic tubing.

The basic principle of operation of this system is that each fluid circuit is filled substantially with water. Because the headset, when in place on the head, is above the reservoirs, water will be forced by gravity downwardly. When, however, the fluid reservoir is compressed, water will be forced up its respective hose and fill and expand its respective balloon. This expansion will cause blockage of the user's ear.

The structure for accomplishing this is shown in detail in FIGS. 12-15. In FIG. 12, it can be seen that each reservoir 130 and 132 is contained within a compartment 146 or 147 in the interior of push button 108. A post 148 extends downwardly from push button 108. Flanges 150 and 151 on opposite sides of push button 108 slide within slots 152 and 154 in case 106. This retains push button 108 within case 106. An H-shaped member 156 has first and second hollow legs 158 and 160 which slide within guides 162 and 164 which extend upwardly from an interior wall 166 of case 106. A cross member 168 extends between legs 158 and 160.

Springs 170 and 172 are captured within legs 158 and 160 and guides 162 and 164 respectively. Springs 170 and 172 are in compression and constantly bias H-shaped member 156 upwardly.

A latch rod 174 is pivotally connected at end 176 to cross member 168 of H-shaped member 156, and extends downwardly through an opening 178 in interior wall 166. Along the length of latch rod 174 is a catch 180.

As seen in FIGS. 12 and 13, a motor 182 is mounted inside case 106 by means known within the art. Motor 182 is electrically communicated with battery 184, also mounted within case 106. The drive axle of motor 182 has at its end a gear 186. A gear rack 188 is rotatable and threadably movable in threaded mounts 190 and 192 which are attached to case 106. Gear 186 of motor 182 moves gear rack 188 linearly in mounts 190 and 192 in a direction depending on the rotation of gear 186.

Furthermore, a fixed nut 194 is positioned on gear rack 188 to the left side of latch rod 174. Latch rod 174 extends downwardly to a location adjacent gear rack 188.

An extension member 196 is connected between push button 108 at the top of case 106 and extends downwardly inside case 106 to a level approximately the same as gear rack 188. A cable 198 is connected between the lower end of extension 196 and gear rack 188.

FIGS. 14 and 15 show the specific structure for ear blocking means 114. (The structure for one side of the headset is shown and described. The structure for the other side is essentially the same.) Hose 110 is secured by clamp 200 to the bottom of the adjustable portion for the headset. A rigid piece 204 is secured to the lower portion of the headset in a transverse or horizontal relationship to the lower portion of the headset. The balloon 142 is then held in position by bracket 208 so that the center of the balloon is basically an abutment or adjacent with the outward extending rigid piece to 204. The relationship of these elements is such that when the headset is in place on the user's head, balloon 142 is positioned between rigid piece 204 on the outside, and the tragus 96 of the user's ear on the inside. Thus, expansion of balloon 142 will push the tragus inwardly to block the auditory canal of the user's ear.

In operation, the embodiment 100 works as follows. The headset is positioned on the user's head so that both balloons are directly adjacent the traguses of each the user's ears. Switch 102 is positioned as desired. When shooting guns, it could be secured by hook and loop fastening material to the user's shoulder. The actuator could be secured to the user's belt or also by hook and loop material to the user's clothing. As discussed previously, the fluid circuit between each reservoir 130 or 132, and the balloons 142 and 144 (not shown), is almost substantially filled with water.

As shown in FIG. 13, H-shaped member 156 is normally biased upwardly to compress reservoirs 130 and 132. Therefore, in the normal state, embodiment 100 forces water through hoses 110 and 112 to balloons 142 and 144 (not shown) to fill or expand them slightly to a position whereby the tragus of each ear of the user is pushed into the auditory canal. To allow non-blocked hearing, push button 108 is pushed downwardly to set the unit. By referring to FIG. 13, downward movement of push button 108 causes post 148 of push button 108 to contact cross member 168 of H-shaped member 156. This in turn causes H-shaped member 156 to be pushed downwardly against the biasing forces of springs 170 and 172. As this occurs, catch 180 of latch rod 174 moves downwardly through opening 178. A spring mechanism 212 is always exerting bias (right to left in FIGS. 12 and 13) against latch rod 174. Catch 180 would then move over the left side of opening 178 in FIGS. 12 and 13 and latch into the position shown in FIG. 12. Release of push button 108 will then cause actuator 104 to be in the set position shown in FIG. 12. The pressure of H-shaped member 156 on reservoirs 130 and 132 would then be released to an extent allowing gravity to push water out of balloons 142 and 144 (not shown) to deflate the balloons sufficiently that they no longer completely block the user's hearing.

Balloons 142 and 144 (not shown) will remain in this state until switch 102 is activated. When that occurs, motor 182 will operate to move gear rack 188 from left to right in FIGS. 12 and 13. Nut 194 will then at some point abut the left side of the lower end of latch rod 174 and move it laterally to the right to a point where catch 180 is no longer latched onto the underside of interior wall 166. At that point, the upwardly biasing power of springs 170 and 172 will move H-shaped member 156 upwardly. This in turn pushes fluid from reservoirs 130 and 132 into balloons 142 and 144 (not shown) to block the hearing of the user.

It is also noted that embodiment 100 has an automatic return mechanism for gear rack 188. Once push button 108 is released so that it moves to its uppermost position, cable 198 connected to the bottom end of extension 196 will pull gear rack 188 from right to left. Therefore, after motor 182 has ceased operation in moving gear rack 188 from left to right, the upwardly biasing force of springs 170 and 172 against reservoirs 130 and 132 will provide sufficient force for cable 198 to pull gear rack 188 from right to left, even over any frictional forces which are residual in motor 182 when it is not operating. Gear rack 188 is then in position ready for the next operation of actuator 104.

It can therefore be seen that the invention achieves all of its stated objectives. It can further be seen that the device automatically blocks a user's ears once the switch means is shorted. It eliminates any fumbling or cumbersome steps to inserting or removing ear plugs or ear cups over the ears.

It will be appreciated that the present invention can take many forms and embodiments. The true essence and spirit of this invention are defined in the appended claims, and it is not intended that the embodiment of the invention presented herein should limit the scope thereof.

For example, different types of actuators or switches could be used. Also, different means for latching or setting the actuator could be utilized. Still further, for example, the actuator case 44 could be hinged to allow easy access to the interior of actuator 44. Moreover, different types of releasable connections between such things as the switch 14 and pad 53, or actuator 42 and pad 55, could be utilized. The length of cables 40 and any electrical connections can vary according to desire. Case 44 for actuator 42 can be made of various materials including metal or plastic. Other options, forms, and alternatives could also be used with the invention.

What is claimed is:

1. A semiautomatic noise suppression means comprising:
    an actuator means connectable to a power source for controlling ear blocking means;
    an activator means for sending a signal to the actuator means to activate operation of the actuator means;
    a pair of ear blocking means moveable between a first position and a second position;
    the actuator means operatively connected to the ear blocking means so as to move each ear blocking means from the first position to the second position which blocks the ear upon the operation of the actuator means, actuator means including an electrical motor to provide automatic movement of the ear blocking means; and
    the ear blocking means including inwardly projecting plug means which are substantially smaller than the circumference of a user's ear, and can project generally into the user's ear and substantially suppress sound through the auditory canal by generally blocking the auditory canal and forcing the ear flap into the auditory canal.

2. The noise suppression means of claim 1 wherein the activator means comprises two a switching means inserted in an electrical circuit connected to the actuator means, the switching means including two conductive strips moveable between contracting and non-contracting positions, and when in the contacting position creating the signal to the actuator means.

3. The noise suppression means of claim 1 wherein the power source is a battery.

4. The noise suppression means of claim 1 wherein the ear blocking means is connected to a headset means for positioning the ear blocking means on the user's head, the ear blocking means comprising:
    a lower section having two opposite ends, one end pivotally mounted to a headset;
    an upper section having two opposite ends, one end slideably and pivotally mounted to the headset;
    the lower section and the upper section each having a second end pivotally mounted to each other such that the ear blocking means is retracted from the ear when the upper section is slid away from the lower section and the ear blocking means forces the ear flap into the ear when the upper section is slid toward the lower section.

5. The noise suppression means of claim 4 wherein the actuator means is operatively connected to the ear blocking means by a cable; the cable mounted to the end of the upper section of the ear blocking means which is slideably mounted to the headset.

6. The noise suppression means of claim 5 wherein the actuator means is comprised of a lever means, the lever means operatively connected to the cable so as to retract the ear blocking means when the lever means is in the first position and to insert the ear blocking means when the lever means is in the second position;
a stop means for urging the lever means from the first position to the second position; a latching means for maintaining the lever means in the first position; a motor means operatively connected to the lever means whereby when the activator means is closed, the motor means disengages the latching means so as to allow the stop means to urge the lever means from the first position to the second position, the motor means being deactivated after the latching means disengage the lever means.

7. The noise suppression means of claim 1 wherein the ear blocking means comprise resilient expandable balloon means positioned between a rigid piece and the user's ear, whereby inflation or expansion of the balloon forces the ear flap into the ear which suppresses noise to the user's ear.

8. The noise suppression means of claim 7 wherein the actuator means includes a flexible fluid reservoir connected in fluid communication to the balloon means whereby compression of the reservoir causes inflation or expansion of the balloon means.

9. The noise suppression means of claim 8 wherein the reservoir is normally in a compressed or semi-compressed state, but is reduced in compression by the setting of the actuator means which releases compression on the reservoir to release expansion or deflate the balloon means.

10. The noise suppression means of claim 9 wherein the actuator means further comprises a motor, the motor driving a rack and pinion means, a latch means releasable by connection to the rack means, so that operation of the motor can release the latch means causing compression of the reservoir in turn causing noise suppression of the ear.

11. The noise suppression means of claim 10 further comprising a rack means reset including an extension member attached to a reset button at one end, and attached by a flexible cable to the rack means at another end, the release of the reset button causing biasing of the rack means back to an original position.

12. The noise suppression means of claim 7 wherein the rigid member adjacent to the balloon means comprises an extension from a headband laterally of the general axis of the headband.

13. The noise suppression means of claim 7 wherein the activator means comprises a switch means including a first electrically conducting strip and a second electrical conducting strip, each electrical conducting strip associated with a panel which is hingable with regard to one another, yet biased apart from one another, wherein pressure against a panel to cause the panels to come into abutment, brings the conducting strips into contact closing an electrical circuit through the activator means.

14. A noise suppression means comprising:
an actuator means connected to a power source for controlling ear blocking means;
an activator means for sending a signal to the actuator means to activate operation of the actuator means;
a headset;
a pair of ear blocking means, each having an upper section and a lower section;
a lower section of a ear blocking means having two opposite ends, one pivotally mounted to the headgear;
an upper section of the ear blocking means earplug having two opposite ends, one end slideably and pivotally mounted to the headgear;
the lower section and the upper section of each ear blocking means earplug having a second end pivotally mounted to each other such that the ear blocking means earplug is retracted from the ear when the upper section is slid away from the lower section and the ear blocking means forces the ear flap into the ear when the upper section is slid toward the lower section; and
the actuator means operatively connected to the ear blocking means so as to move each ear blocking means from a position retracted from the ear to a position adjacent the ear upon receipt of the signal from the activator means.

15. The noise suppression means of claim 14 wherein the activator means comprises a switching means inserted in an electrical circuit connected to the actuator means, the switching means including two conductive strips moveable between contracting and non-contracting positions, and when in the contacting position creating the signal to the actuator means.

16. The noise suppression means of claim 14 wherein the the activator means comprises a switch means closed by manual pressure against the switch means.

17. The noise suppression means of claim 14 wherein the power source is a battery.

18. The noise suppression means of claim 14 wherein the actuator means is operatically to earplugs by a cable; the cable mounted to the end of the upper section of the ear blocking means which is slideably mounted to the headset.

* * * * *